United States Patent
Haneda et al.

(10) Patent No.: US 6,469,043 B1
(45) Date of Patent: Oct. 22, 2002

(54) SULFONAMIDE-CONTAINING INDOLE COMPOUNDS

(75) Inventors: Toru Haneda; Akihiko Tsuruoka; Junichi Kamata; Tadashi Okabe; Keiko Takahashi; Kazumasa Nara; Shinichi Hamaoka; Norihiro Ueda; Takashi Owa; Toshiaki Wakabayashi; Yasuhiro Funahashi; Taro Semba; Naoko Hata; Yuji Yamamoto; Yoichi Ozawa; Noako Tsukahara, all of Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/647,215
(22) PCT Filed: Feb. 24, 2000
(86) PCT No.: PCT/JP00/01071
§ 371 (c)(1), (2), (4) Date: Sep. 28, 2000
(87) PCT Pub. No.: WO00/50395
PCT Pub. Date: Aug. 31, 2000

(30) Foreign Application Priority Data

Feb. 26, 1999 (JP) .......................................... 11-049870

(51) Int. Cl.[7] ..................... A61K 31/404; C07D 209/04
(52) U.S. Cl. ..................... 514/414; 514/444; 514/428; 548/469; 548/467; 548/490; 548/509
(58) Field of Search ................. 514/414, 444, 514/428; 548/469, 490, 509, 467

(56) References Cited

FOREIGN PATENT DOCUMENTS

| EP | 673937 | * | 3/1995 |
| JP | A8231505 | | 9/1996 |
| JP | 08231505 | * | 9/1996 |
| JP | A9316053 | | 12/1997 |
| WO | 9301182 | * | 1/1993 |
| WO | 9507276 | * | 3/1995 |
| WO | A1-9507276 | | 3/1995 |
| WO | A1-9730706 | | 8/1997 |
| WO | WO 01 56607 | | 8/2001 |

* cited by examiner

Primary Examiner—Mukund J. Shah
Assistant Examiner—Sudhaker B Patel
(74) Attorney, Agent, or Firm—Birch, Stewart, Kolasch & Birch, LLP.

(57) ABSTRACT

The present invention creates a novel antiangiogenic agent and provides an antitumor agent which shows high safety as compared with conventional antitumor agents, has a sure effect and is able to be administered for a long period. That is, it provides an indole compound represented by the following formula (I), its pharmacologically acceptable salt or hydrates thereof.

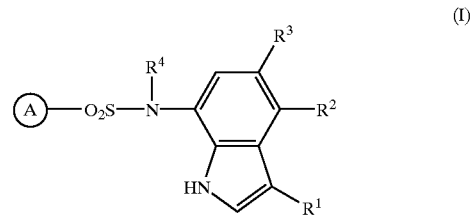

(I)

In the formula, $R^1$ represents hydrogen atom, a halogen atom or cyano group; $R^2$ and $R^3$ are the same as or different from and each represents hydrogen atom, a $C_1$~$C_4$ lower alkyl group or a halogen atom; $R^4$ represents hydrogen atom or a $C_1$~$C_4$ lower alkyl group; and the ring A represents cyanophenyl group, aminosulfonylphenyl group, aminopyridyl group, aminopyrimidyl group, a halopyridyl group or cyanothiophenyl group, provided that the case where all of $R^1$, $R^2$ and $R^3$ are hydrogen atoms, where both $R^2$ and $R^3$ are hydrogen atoms or where the ring A is aminosulfonyl group and both $R^1$ and $R^2$ are halogen atoms is excluded. Further, when the ring A is cyanophenyl group, 2-amino-5-pyridyl group or a 2-halo-5-pyridyl group and $R^1$ is cyano group or a halogen atom, at least one of $R^2$ and $R^3$ should not be a hydrogen atom.

22 Claims, No Drawings

SULFONAMIDE-CONTAINING INDOLE COMPOUNDS

This application is the national phase under 35 U.S.C. § 371 of PCT International Application No. PCT/JP00/01071 which has an International filing date of Feb. 24, 2000, which designated the United States of America.

FIELD OF THE INVENTION

The present invention relates to a sulfonamide-containing indole compound and to an antiangiogenic effect thereof. More particularly, it relates to an antitumor agent, a cancer metastasis suppressor, a therapeutic agent for diabetic retinopathy, a therapeutic agent for rheumatic arthritis and a therapeutic agent for hematoma on the basis of an antiangiogenic effect.

PRIOR ART

It has become clear that there is a close relation between proliferation of cancer and angiogenesis. Thus, when angiogenesis is not generated at the site of cancer, the cancer remains in a state of dormant tumor. However, it has become clarified that, when angiogenesis is generated, oxygen and nutrients in blood are supplied to the tumor whereby proliferation and metastasis of cancer are promoted resulting in a clinically malignant state. Accordingly, it is expected that, when angiogenesis of cancer is suppressed, proliferation and metastasis of cancer can be suppressed. Since angiogenetic vessels are composed of endothelial cells and interstitial cells of the host, target of the antiangiogenic agent is not cancer cells but such normal cells of the host. Because of the fact that the cancer cells are not a direct target, efficacy to the cancer which does not respond to known anticancer agents can be expected as well and, in addition, it is presumed that the possibility of occurrence of tolerant cancer which is a big problem in cancer therapy is little. In addition, angiogenesis is a tumor-specific phenomenon and, in mature individuals, it is limited to the formation of endometrium, etc. accompanied by a menstrual cycle. Accordingly, its adverse effect is thought to be little as compared with known anticancer drugs. Recently, it has been experimentally proved in preclinical tests that antiangiogenic agents are able to suppress and further to reduce the proliferation of cancer in the cancer-transplanted models and that tolerant cancer is not generated and, in clinical tests, the correlation between angiogenesis and malignization of many solid cancers such as breast cancer, prostatic cancer, lung cancer and cancer of the colon has been shown.

In cancer tissues, apoptosis and proliferation of cancer cells continuously occur and it has been known that, depending upon the balance between them, progressive cancer or dormant tumor results. An antiangiogenic agent does not directly kill the cancer cells but cuts off the nutrient sources so that the said balance is inclined to apoptosis inducing dormant tumor or reduction in cancer whereby it is a drug which can be expected to exhibit an excellent effect (prolongation of life, inhibition of recurrence and suppression of metastasis) by a long-term therapy.

In a preclinical stage, there are antiangiogenic agents by various action mechanisms but, since their antitumor effect in a preclinical stage is insufficient, their usefulness in clinical stage is still doubtful and, therefore, there has been a brisk demand for antiangiogenic agents where the effect is reliable.

It has been also known that angiogenesis participates in retinopathy or retinitis. When blood vessel is proliferated in retina, eyesight gets worse and, when progressed, blindness is resulted. There has been no effective therapeutic drug therefor at present and effective therapeutic drugs have been demanded.

WO 9301182 discloses antitumor agents due to a specific tyrosine kinase inhibiting activity of the compounds having an indole skeleton but they are indolylmethylene-2-indolinone compounds and are different from the present invention. Similarly, WO 964016 discloses an antitumor agent due to a specific tyrosine kinase inhibiting activity of the compounds having an indole skeleton but they are 2-indolinone-3-methylene compounds and are different from the present invention. Sulfonamide compounds having an indole structure are disclosed in JP-A 7-165708 and JP-A 8-231505. However, the compounds which are specifically disclosed in JP-A 7-165708 and have two substituents other than aryl (or heteroaryl) sulfonylamino group on an indole ring are limited and combinations of those substituents are only six, i.e. (1) 3-Cl and 4-Cl; (2) 3-Cl and 4-OCH$_3$; (3) 3-Cl and 4-OH; (4) 3-Cl and 4-CH$_3$; (5) 3-Cl and 4-CN; and (6) 3-CN and 5-Br. There is no combination of (a) 3-CN and 4-CH$_3$; (b) 3-Cl and 5-Br; (c) 3-Cl and 4-Br; and (d) 3-Br and 4-CH$_3$. With regard to 4-halogen monosubstituted compounds, there is a description for 4-Br compounds but its sulfonyl moiety is a p-nitrophenol compound only. Further, indole compounds disclosed in JP-A 8-231505 are 3-halogen or 3-cyano monosubstituted compounds only. In those laid-open publications, there is no description for an antiangiogenic effect at all and there is no description suggesting that as well.

DISCLOSURE OF THE INVENTION

An object of the present invention is to create a novel antiangiogenic agent and to provide an antitumor agent which shows a high safety and a sure effect as compared with conventional antitumor agents and is able to be administered for a long period.

The present inventors have carried out an intensive study, found that the sulfonamide-containing indole compound represented by the following formula achieves the aimed object and accomplished the present invention. That is, the present invention relates to a sulfonamide-containing indole compound represented by the following formula (I), its pharmacologically acceptable salt or hydrates thereof.

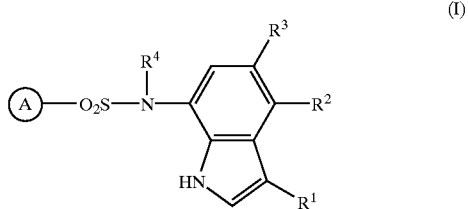

(I)

In the formula, R$^1$ represents hydrogen atom, a halogen atom or cyano group; R$^2$ and R$^1$ are the same as or different from and each represents hydrogen atom, a C$_1$~C$_4$ lower alkyl group or a halogen atom; R$^4$ represents hydrogen atom or a C$_1$~C$_4$ lower alkyl group; and the ring A represents cyanophenyl group, aminosulfonylphenyl group, aminopyridyl group, aminopyrimidyl group, halopyridyl group or cyanothiophenyl group, provided that the case where all of R$^1$, R$^2$ and R$^3$ are hydrogen atoms, where both R$^2$ and R$^3$ are hydrogen atoms, or where the ring A is aminosulfonyl group and both R$^1$ and R$^2$ are halogen atoms is excluded. Further, when the ring A is cyanophenyl group, 2-amino-5-pyridyl group or a 2-halo-5-pyridyl group and $R^1$ is cyano group or a halogen atom, at least one of $R^2$ and $R^3$ should not be a hydrogen atom.

The present invention relates to a method for the prevention or therapy of the disease against which inhibitory of angiogenesis at the site of tumor, rheumatic arthritis or diabetic retinopathy is effective for the prevention or therapy, by administering a pharmacologically effective dose of the above-mentioned indole compound, its pharmacologically acceptable salt or hydrates thereof to a patient.

The present invention further relates to a use of the above-mentioned indole compound, its pharmacologically acceptable salt or hydrates thereof for the manufacture of a preventive or therapeutic agent for the disease against which an antiangiogenic agent is effective for the prevention or therapy.

The present invention furthermore relates to an antiangiogenic agent, an antitumor agent, a therapeutic agent for pancreatic cancer, a therapeutic agent for cancer of the colon, a therapeutic agent for gastric cancer, a therapeutic agent for breast cancer, a therapeutic agent for prostatic cancer, a therapeutic agent for lung cancer, a therapeutic agent for ovarian cancer, a cancer metastasis suppressor, a therapeutic agent for diabetic retinopathy, a therapeutic agent for rheumatic arthritis or a therapeutic agent for hematoma, which comprises the above-mentioned indole compound, its pharmacologically acceptable salt or hydrates thereof as an effective ingredient. It relates to a method for prevention, therapy and improvement by use of any of those pharmaceutical agents. Further, it relates to a use of the above compound for the manufacture of any of those pharmaceutical agents.

In the above formula (I), a halogen atom means fluorine atom, chlorine atom, bromine atom or iodine atom. A $C_1$~$C_4$ lower alkyl group means a linear or branched alkyl group such as methyl group, ethyl group, n-propyl group, n-butyl group, iso-propyl group, iso-butyl group and tert-butyl group.

The indole compound represented by the above formula (I) may form a salt with an acid or with a base. The present invention also includes a salt of the indole compound (I) as well. Examples of the salt with an acid are an inorganic acid salt such as hydrochloride, hydrobromide or sulfate and that with an organic acid such as acetic acid, lactic acid, succinic acid, fumaric acid, maleic acid, citric acid, benzoic acid, methanesulfonic acid or p-toluenesulfonic acid. Examples of the salt with a base are an inorganic salt such as sodium salt, potassium salt or calcium salt and that with an organic base such as triethylamine, arginine or lysine.

It goes without saying that all hydrates of such a compound and of its pharmacologically acceptable salt are included. Although the compounds of the present invention show a strong antiangiogenic effect, compounds which are subjected to metabolism such as oxidation, reduction, hydrolysis and conjugation in vivo are also included. The present invention further includes the compounds which produce the compound of the present invention as a result of metabolism such as oxidation, reduction and hydrolysis in vivo.

The compound of the present invention (I) can be manufactured by various methods and representative ones among them will be as follows.

It can be manufactured by the reaction of a sulfonic acid represented by the formula (II):

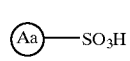

(II)

(in the formula, the ring Aa represents cyanophenyl group, aminosulfonylphenyl group, aminopyridyl group, aminopyrimidyl group, a halopyridyl group or cyanothiophenyl group) or a reactive derivative thereof with a compound represented by the formula (III):

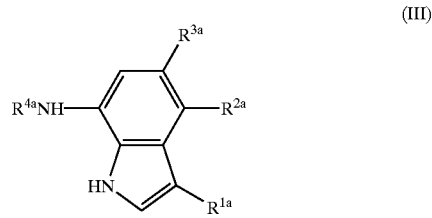

(III)

(in the formula, $R^{1a}$ represents hydrogen atom, a halogen atom or cyano group; and $R^{2a}$ and $R^{3a}$ are the same as or different from and each represents hydrogen atom, a $C_1$~$C_4$ lower alkyl group or a halogen atom, provided that the case where all of $R^{1a}$, $R^{2a}$ and $R^{3a}$ are hydrogen atoms or where both $R^{2a}$ and $R^{3a}$ are hydrogen atoms is excluded).

Examples of the reactive derivative of the sulfonic acid (II) are commonly and well utilized reactive derivatives such as sulfonyl halide, sulfonyl acid anhydride and N-sulfonylimidazolide and the particularly advantageous example is a sulfonyl halide. Although there is no particular limitation for the solvent used for the reaction, those which dissolve the material substances and do not readily react with them are preferred. For example, pyridine, tetrahydrofuran, dioxane, benzene, ethyl ether, dichloromethane, dimethylformamide and a mixed solvent consisting of two or more which are selected from them can be used. In addition, when an acid is liberated with a progress of the reaction as in the case of using a sulfonyl halide in the reaction, it is preferred to conduct the reaction in the presence of an appropriate deacidifying agent and, therefore, the use of a basic solvent such as pyridine is particularly appropriate. When a neutral solvent is used, a basic substance such as an alkali carbonate or an organic tertiary amine may be added. of course, the solvent which can be used is not limited to those listed here. Usually, the present reaction proceeds at room temperature but, if necessary, it may be cooled or heated. The reaction time is usually from 10 minutes to 20 hours and is optionally selected depending upon the type of the material compounds and the reaction temperature.

When an amino group is protected in the resulting product, a conventional deprotecting method such as treatment with an acid, treatment with an alkali and catalystic reduction may be carried out upon necessity whereby it is possible to give an indole compound (I) having a free amino group.

Now, methods for the manufacture of the starting compounds (II), reactive derivative thereof and (III) used in the present invention will be illustrated.

The starting compound (II) and reactive derivative thereof include both known compounds and novel compounds. In the case of novel compounds, they can be manufactured by applying the already-reported synthetic method for known compounds or by combining them. For example, novel sulfonyl chloride may be manufactured by a method applying the synthetic methods mentioned in Chem. Ber., 90, 841

(1957); J. Med. Chem., 6, 307 (1963); J. Chem. Soc. (c), 1968, 1265; Chem. Lett., 1992, 1483; J. Am. Chem. Soc., 59, 1837 (1937); J. Med. Chem., 23, 1376 (1980); J. Am. Chem. Soc., 70, 375 (1948); J. Am. Chem. Soc., 78, 2171 (1956) etc.

When $R^{1a}$ and $R^{3a}$ are hydrogen atoms and $R^{2a}$ is a halogen atom in the starting compound (III), it can be manufactured by a known synthetic method. When $R^{2a}$ and $R^{3a}$ are the same as or different from and each represents hydrogen atom, a $C_1$~$C_4$ lower alkyl group or a halogen atom (the case where both are hydrogen atoms is excluded) and $R^{1a}$ is cyano group, it can be manufactured as follows.

Reaction Formulae 1

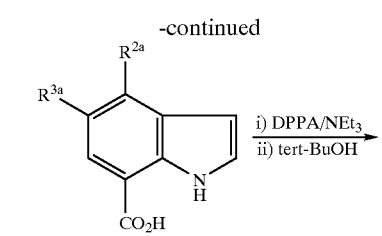
(a)

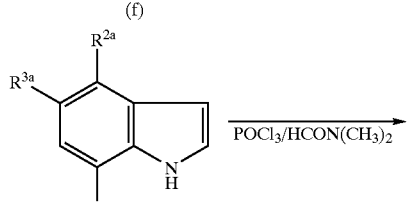
(b)

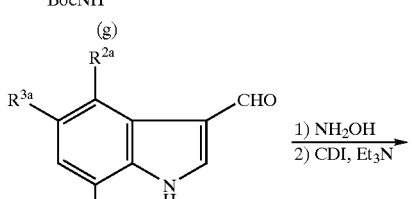
(c)

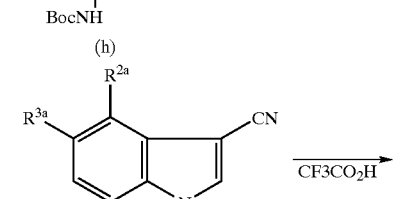
(d)

In the formulae, $R^{1a}$, $R^{2a}$ and $R^{3a}$ have the same meanings as defined above.

Reaction Formulae 2

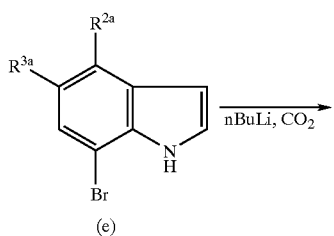
(e)

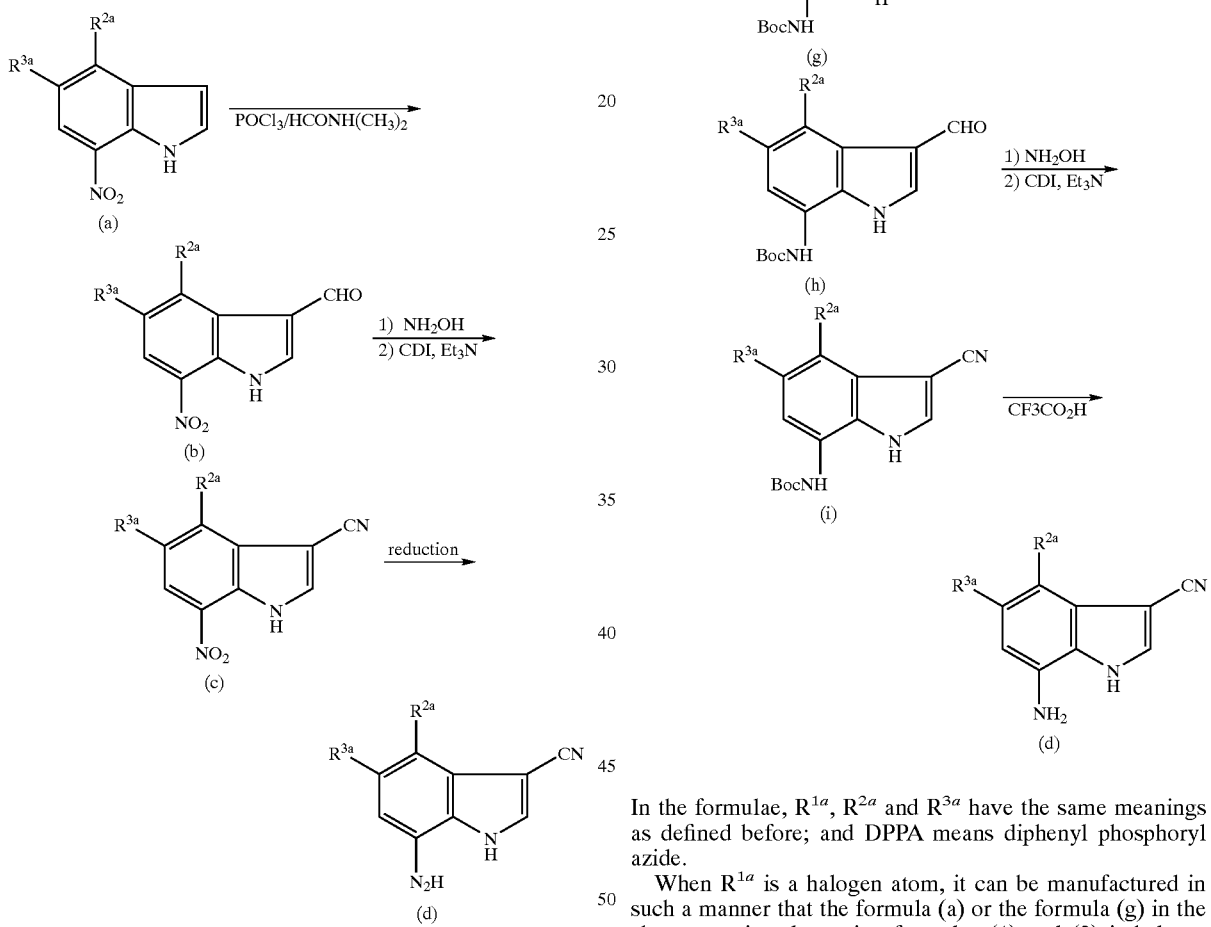

In the formulae, $R^{1a}$, $R^{2a}$ and $R^{3a}$ have the same meanings as defined before; and DPPA means diphenyl phosphoryl azide.

When $R^{1a}$ is a halogen atom, it can be manufactured in such a manner that the formula (a) or the formula (g) in the above-mentioned reaction formulae (1) and (2) is halogenated by a conventional means and the nitro group is reduced or a protecting group of an amino group is eliminated.

When the compound of the present invention is used as a medicament, it is administered either orally or parenterally. The dose varies depending upon degree of the symptom, age, sex, body weight and sensitivity difference of the patient, method of the administration, period for the administration, interval of the administration, property of the pharmaceutical preparation, type of the preparation, type of the effective ingredients etc., and is not particularly limited. In the case of intravenous administration, it is 1–2000 mg, preferably 1–1500 mg and, more preferably, 5–1000 mg while, in the case of oral administration, it is usually 10–6000 mg, preferably about 50–4000 mg and, more preferably, 100–3000 mg per day for adults, and that is usually administered once daily or by dividing into up to three times a day.

When a solid preparation for oral administration is prepared, filler and, if necessary, binder, disintegrating agent, lubricant, coloring agent, corrigent, etc. are added to the main ingredient, followed by subjecting to a common method to make into tablets, coated tablets, granules, fine granules, powders, capsules etc.

Examples of the filler are lactose, corn starch, sucrose, glucose, sorbitol, crystalline cellulose and silicon dioxide; examples of the binder are polyvinyl alcohol, ethyl cellulose, methyl cellulose, gum arabic, hydroxypropyl cellulose and hydroxypropyl methyl cellulose; examples of the lubricant are magnesium stearate, talc and silica; examples of the coloring agent are those which are allowed to add to the pharmaceuticals; and examples of the flavoring agents are cacao powder, menthol, aromatic, peppermint oil, borneol, and cinnamon powder. It is of course no problem that such tablets and granules are appropriately coated with a sugar coat, gelatin coat or others if necessary.

In preparing the injection, a pH adjusting agent, a buffer, a suspending agent, a solubilizer, a stabilizer, an isotonizing agent, a preservative, etc. are added, if necessary, to the main ingredient followed by subjecting to a conventional method to make into injections for intravenous, subcutaneous or intramuscular administration. At that time, it may be made into a freeze-dried product by a common method if necessary.

Examples of the suspending agent are methyl cellulose, polysorbate 80, hydroxyethyl cellulose, gum arabic, tragacanth powder, sodium carboxymethyl cellulose and polyoxyethylene sorbitan monolaurate.

Examples of the solubilizer are polyoxyethylene hydrogenated castor oil, polysorbate 80, nicotinamide, polyoxyethylene sorbitan monolaurate, macrogol and castor oil fatty acid ethyl ester.

Examples of the stabilizer are sodium sulfite and sodium metasulfite. Examples of the preservative are methyl parahydroxybenzoate, ethyl para-hydroxybenzoate, sorbic acid, phenol, cresol and chlorocresol.

Effect of the compounds of the present invention will be shown by way of the following pharmacological experimental examples.

Pharmacological Experimental Example 1
Antiangiogenic Effect

The inhibition degree of angiogenesis which was observed when aorta pieces of rat were incubated in collagen was defined as an antiangiogenic effect. That is, the aorta excised from male rat of Sprague-Dawley strain (10–12 weeks age) was washed with a Hanks' solution so that fat tissues around there were removed minutely. The aorta was incised to prepare pieces of 2 mm square and they were allowed to stand in a 24-well plate holding the endothelial cells upside. Then, 500 μl of neutralized Type I collagen (Cell Matrix Type I-A; manufactured by Nitta Gelatin) were poured over each well and allowed to stand at room temperature for about 20 minutes in a clean bench to solidify the gel. After confirming that the gel was solidified, 500 μl of MCDB 131 medium (manufactured by Chlorella Kogyo) were added thereto followed by incubating in a $CO_2$ incubator (5% $CO_2$) at 37° C. On the next day, the culture medium was exchanged with 500 μl of MCDB 131 medium containing the test compound and the incubation was continued. After three days, the medium was again exchanged with 500 μl of MCDB 131 medium containing the test compound and, at the stage of the 7th day from the initiation of addition of the test compound, numbers of capillaries formed around the aorta were counted under a microscope. The solution containing the test compound was prepared in a three-fold dilution system where 10 μg/ml was the highest concentration.

Inhibiting rate was calculated from the following formula and 50% inhibiting concentration ($IC_{50}$) for each test compound was determined.

Inhibiting Rate $(\%)=(C-T)/C\times 100$

C: Numbers of capillaries when no compound was added
T: Numbers of capillaries when a compound was added

TABLE 1

| Test Compound (Ex. No.) | $IC_{50}$ Value (μg/ml) |
|---|---|
| Example 1 | 0.08 |
| Example 2 | 0.07 |
| Example 3 | 0.10 |
| Example 4 | 0.10 |
| Example 5 | 0.15 |
| Example 6 | 0.06 |
| Example 7 | 0.42 |
| Example 8 | 0.05 |
| Example 9 | 0.05 |
| Example 10 | 0.06 |

Pharmacological Experimental Example 2
Inhibitory Effect of Growth of Endothelial Cells Endothelial cells derived from human umbilical vein (HUVEC; manufactured by Sanko Junyaku) incubated in an EGM medium (manufactured by Sanko Junyaku) containing 100 Units of penicillin and 100 μg/ml of streptomycin were adjusted to $0.8-1\times10^4$ cells/ml and each 100 μl were separately placed on a 96-well plate. After incubating in a $CO_2$ incubator (5% $CO_2$) at 37° C. overnight, 100 μl of EGM medium containing test compound diluted in a three-fold manner were added thereto followed by incubating for three days. The cell numbers at that time were measured by MTT method. That is, 50 μl of phosphate buffer containing 0.33% of 3-(4,5-dimethylthiazol-2-yl)-2,5-diphenyltetrazolium bromide (MTT) was added thereto and incubation was continued for 3–4 hours. Then, after the supernatant liquid of the culture was removed, 100 μl of dimethyl sulfoxide (DMSO) was added to dissolve a formazane which was formed in the cells and the absorbance at the wave length of 540 nm was measured by use of plate reader (manufactured by Corona Denki).

Inhibiting rate was calculated from the following formula and 50% inhibiting concentration ($IC_{50}$) was determined for each compound.

Inhibition Rate $(\%)=(C-T)/C\times 100$

C: Absorbance when no compound was added
T: Absorbance when a compound was added

TABLE 2

| Test Compound (Ex. No.) | $IC_{50}$ Value (μg/ml) |
|---|---|
| Example 1 | 0.10 |
| Example 2 | 0.12 |
| Example 3 | 0.62 |
| Example 4 | 1.3 |
| Example 5 | 0.98 |

TABLE 2-continued

| Test Compound (Ex. No.) | IC$_{50}$ Value (μg/ml) |
| --- | --- |
| Example 6 | 1.2 |
| Example 7 | 0.98 |
| Example 8 | 0.49 |
| Example 9 | 1.6 |
| Example 10 | 0.38 |

Pharmacological Experimental Example 3
Inhibitory Effect of Proliferation of Mouse B16 Melanoma Mouse B16 melanoma cells incubated in a Dulbecco-modified Eagle medium (DMED; manufactured by Nissui Seiyaku) containing 10% of fetal bovine serum, 100 Units/ml of penicillin and 100 μg/ml of streptomycin were adjusted to 2×10$^4$ cells/ml and each 100 μl thereof were separately placed on a 96-well plate. After an incubation was carried out in a CO$_2$ incubator (5% CO$_2$) at 37° C. for one night, then 100 μl of the above culture containing a test compound diluted in a 3-fold series were added thereto followed by incubating for 3 days and the cell numbers at that time were measured by an MTT method. Incidentally, a treatment with a 0.33% MTT solution was carried out for 1–2 hour(s).

Inhibiting rate was calculated from the following formula and 50% inhibiting concentration (IC$_{50}$) was determined for each compound.

Inhibiting Rate (%)=(C−T)/C×100

C: Absorbance when no compound was added
T: Absorbance when a compound was added

TABLE 3

| Test Compound (Ex. No.) | IC$_{50}$ Value (μg/ml) |
| --- | --- |
| Example 1 | 10 |
| Example 2 | 15 |
| Example 3 | 21 |
| Example 4 | 19 |
| Example 5 | 8.8 |
| Example 6 | 6.5 |
| Example 7 | 7.5 |
| Example 8 | 19 |
| Example 9 | 8.4 |
| Example 10 | 23 |

It is apparent from Pharmacological Experimental Example 1 that the compounds of the present invention exhibit a clear antiangiogeneic effect. It is apparent from Pharmacological Experimental Examples 2 and 3 that the proliferation inhibitory effect of the compounds of the present invention on B16 melanoma cells was 5 to 100-fold weaker than that on endothelial cells and accordingly that they specifically act the endothelial cells in blood vessel.

In the meanwhile, evaluation of an antitumor effect was carried out in accordance with a method of Koyanagi, et al. (*Cancer Res.*, 54, 1702–1706, 1994) using a KP-1 cell strain derived from human pancreatic cancer and an HCT 116 cell strain derived from human cancer of the colon. The above-mentioned human cancer cells (5×10$^6$ cells) were subcutaneously transplanted to nude mice (KSN) of 6 to 7 weeks age and, since the stage where it became to the size of about 100 mm$^3$, administration of the compound of the present invention was started. In the experiments, ten mice were used for a group to which no drug was administered while, in a drug-administered group, five mice were used for each dose. The dose of 50 mg/kg, 100 mg/kg or 200 mg/kg was continuously administered per os two times a day and the size of the tumor on the 22nd day from the beginning of the administration was compared with that in the group to which no drug was administered. The result was 37%, 30% and 11%, respectively in the KP-1 cell strain derived from human pancreatic cancer and 0.2%, 0.3% and 0.0%, respectively in the HCT 116 cell strain derived from human cancer of the colon in the case of a group to which the compound of Example 1 was administered for example. Thus, the compound of Example 1 showed a significant antitumor effect.

From the above results, the compound of the present invention can be expected to exhibit an excellent effect in view of efficacy and safety as compared with the known bactericidal antitumor agents which directly target cancer cells.

As noted in the above Experimental Examples, the compounds of the present invention have an excellent antiangiogenic effect and are useful as antitumor agents for pancreatic cancer, cancer of the colon, gastric cancer, bread cancer, prostatic cancer, lung cancer and ovarian cancer and also as therapeutic agents for diabetic retinopathy, rheumatic arthritis and hematoma.

EXAMPLES

Hereinafter, Production Examples for showing the manufacture of the material compounds for the compounds of the present invention and Examples for showing the compounds of the present invention will be illustrated although it goes without saying that the present invention is not limited thereto.

Production Example 1

Ethyl pyruvate N-(5-methyl-2-nitrophpnyl) hydrazone

To a mixed solution of 160 ml of water and 170 ml of concentrated hydrochloric acid was added 75.0 g (493 mmol) of 5-methyl-2-nitroaniline followed by stirring. An aqueous solution (80 ml) of 36.0 g (517 mmol) of sodium nitrite was added dropwise thereinto at −20° C. The reaction solution was added to a solution which was prepared by dissolving ethyl 2-methylacetacetate in 100 ml of ethanol followed by adding 200 ml of a 12N aqueous solution of potassium hydroxide, at −20° C. with stirring during 30 minutes. After the mixture was stirred at the same temperature for 30 minutes, 100 ml of concentrated hydrochloric acid were added and the resulting precipitates were collected by filtration, washed with water and dried in vacuo for overnight. A mixed solution of diethyl ether and hexane was added thereto, and the resulting crystals were collected by filtration to give 130 g of the title compound.

$^1$H-NMR (DMSO-d$_6$) δ (ppm); 1.29(3H, t, J=7.2 Hz), 2.16(3H, s), 2.40(3H, s), 4.25(2H, q, J=7.2 Hz), 6.91(1H, dd, J=8.8, 2.0 Hz), 7.63(1H, s), 8.07(1H, d, J=8.8 Hz), 10.69 (1H, s).

Production Example 2

Ethyl 4-methyl-7-nitro-1H-indole-2-carboxylate

To 250 ml of a suspension of 25.0 g (94.2 mmol) of the compound of Production Example 1 in xylene was added 100 g of polyphosphoric acid followed by heating under reflux for 3 hours. To the reaction solution were added 80 ml of water and 300 ml of ethyl acetate under ice-cooling. The resulting insoluble matters were filtered off followed by washing with 1.5 liters of ethyl acetate, and the resulting filtrate was extracted with ethyl acetate. The organic layer was successively washed with a saturated sodium bicarbonate solution, water and brine, dried over magnesium sulfate and concentrated to dryness. To the resulting residue was added a mixed solution of tert-butyl methyl ether and hexane, and the resulting crystals were collected by filtration to give 11.1 g of the title compound.

$^1$H-NMR (DMSO-$d_6$) δ (ppm); 1.35(3H, t, J=7.2 Hz), 2.65(3H, s), 4.38(2H, q, J=7.2 Hz), 7.16(1H, d, J=8.4 Hz), 7.51(1H, s), 8.19(1H, d, J=8.4 Hz), 11.29(1H, br s).

Production Example 3

4-Methyl-7-nitron-1H-indole-2-carboxylic Acid

To 150 ml of a solution of 11.0 g (44.3 mmol) of the compound of Production Example 2 in tetrahydrofuran was added 150 ml of a 1N aqueous solution of sodium hydroxide followed by heating under stirring at 80° C. for 30 minutes. The reaction solution was concentrated, 40 ml of 5N hydrochloric acid was added to the resulting residue under ice-cooling to adjust to pH 1, and the resulting precipitates were filtered and washed with water. The precipitates were dissolved in 300 ml of tetrahydrofuran and extracted with ethyl acetate. The organic layer was washed with brine, dried over magnesium sulfate and concentrated to dryness to give 9.60 g of the title compound.

$^1$H-NMR (DMSO-$d_6$) δ (ppm); 2.62(3H, s), 7.13(1H, d, J=8.0 Hz), 7.42(1H, S), 8.15(1H, d, J=8.0 Hz), 11.00(1H, brs).

Prduction Example 4

4-Methyl-7-nitro-1H-indole

Into 60 ml of 1,3-dimethyl-2-imidazolidinone was dissolved 9.58 g (43.5 mmol) of the compound of Production Example 3, 1.04 g (4.35mmol) of basic copper carbonate was added thereto and the mixture was heated under stirring at 180° C. for 4 hours. To the reaction solution was added 120 ml of ethyl acetate under ice-cooling, the resulting insoluble matters were filtered off and the resulting filtrate was extracted with ethyl acetate. The organic layer was washed with water and brine successively and dried over magnesium sulfate. After the concentration, the resulting residue was purified by a silica gel column chromatography to give 4.87 g of the title compound.

$^1$H-NMR (DMSO-$d_6$) δ (ppm); 2.59(3H, s), 6.74(1H, s), 7.03(1H, d, J=8.4 Hz), 7.48(1H, s), 8.00(1H, d, J=8.4 Hz), 11.86(1H, brs).

Production Example 5

3-Formyl-4-methyl-7-nitro-1H-indole

To 12 ml (154 mmol) of dimethylformamide was added 1.5 ml (16.1 mmol) of phosphorus oxychloride at 0° C. in a nitrogen atmosphere followed by stirring at room temperature at the same temperature for 20.5 hours. A solution (20 ml) of 2.0 g (11.4 mmol) of the compound of Production Example 4 in dimethylformamide was added thereto at 0° C. followed by heating at 90° C. for 21 hours under stirring. To the reaction solution was added 100 ml of a 1N aqueous solution of sodium hydroxide under ice-cooling followed by extracting with ethyl acetate. The organic layer was washed with water and brine successively, dried over magnesium sulfate and concentrated to dryness. To the resulting residue was added a mixed solution of tert-butyl methyl ether and hexane and the resulting crystals were collected by filtration to give 2.23 g of the title compound.

$^1$H-NMR (DMSO-$d_6$) δ (ppm); 2.90(3H, s), 7.21(1H, d, J=8.4 Hz), 8.11(1H, d, J=8.4 Hz), 8.39(1H, s), 10.01(1H, s), 12.71(1H, brs).

Production Example 6

3-Cyano-4-methyl-7-nitron-1H-indole Into 100 ml of dimethylformamide was dissolved 2.21 g (10.8 mmol) of the compound of Production Example 5 followed by adding 900 mg (13.0 mmol) of hydroxylamine hydrochloride and 1.05 ml (13.0 mmol) of pyridine thereto. After heating at 60° C. under stirring for 40 minutes, 53.9 mmol of 1,1'-carbonyldiimidazole (53.9 mmol) were added to the reaction solution under ice-cooling. After heating at 60° C. for further 30 minutes under stirring, 3.0 ml (21.5 mmol) of triethylamine was added to the reaction solution followed by heating at the same temperature for further 1 hour under stirring. To the reaction mixture was added 50 ml of ice water under ice-cooling followed by extracting with ethyl acetate. The organic layer was washed with water and brine successively, dried over magnesium sulfate and concentrated to dryness. To the resulting residue was added a mixed solution of tert-butyl methyl ether and hexane, and the resulting crystals were collected by filtration to give 1.95 g of the title compound.

$^1$H-NMR (DMSO-$d_6$) δ (ppm); 2.78(3H, s), 7.22(1H, d, J=8.0 Hz), 8.14(1H, d, J=8.0 Hz), 8.41(1H, s), 12.76(1H, brs).

Production Example 7

7-Bromo-4-methyl-1H-indole

To 300 ml of a solution of 65.0 g (301 mmol) of 2-bromo-5-methylnitrobenzene in tetrahydrofuran was added 1 liter of a 1.0M solution of vinyl magnesium bromide (1 mol) in tetrahydrofuran at −60° C. in a nitrogen atmosphere under stirring during 1 hour. To the reaction mixed solution were added a saturated aqueous solution of ammonium chloride and ethyl acetate, and the resulting insoluble matters were filtered off. The resulting filtrate was dried over magnesium sulfate, concentrated, and then the resulting residue was purified by a silica gel column chromatography to give 35.5 g of the title compound.

$^1$H-NMR (DMSO-$d_6$) δ (ppm); 2.42(3H, s), 6.55(1H, s), 6.73(1H, d, J=7.6 Hz), 7.16(1H, d, J=7.6 Hz), 7.35(1H, s), 11.24(1H, brs).

Production Example 8

4-Methyl-1H-indole-7-carboxylic Acid

To a solution (200 ml) of 35.5 g (169 mmol) of the compound of Production Example 7 in tetrahydrofuran was added a 1.6M solution (350 ml) of butyl lithium (384 mmol) in hexane in a nitrogen atmosphere at −78° C. under stirring. After stirring for 40 minutes under ice-cooling, carbon dioxide was introduced to the reaction solution at −50° C. and stirred as it was for 15 minutes. Water was added to the reaction mixture at the same temperature, the solvent was evaporated and the resulting precipitates were collected by filtration and washed with water. The precipitates were dissolved in 300 ml of tetrahydrofuran, dried over magnesium sulfate and then concentrated to dryness to give 25.9 g of the title compound.

$^1$H-NMR (DMSO-d$_6$) δ (ppm); 2.51(3H, s), 6.53(1H, s), 6.88(1H, d, J=7.6 Hz), 7.31(1H, s), 7.62(1H, d, J=7.6 Hz), 10.99(1H, brs), 12.79(1H, brs).

Production Example 9

7-(N-tert-Butoxcarbonyl)amino-4-methyl-1H-indole

In 80 ml of toluene was suspended 7.0 g (40.0 mmol) of the compound of Production Example 8, then 22 ml (160 mmol) of triethylamine and 11.2 ml (52 mmol) of diphenylphosphoryl azide were added thereto in a nitrogen atmosphere and the mixture was stirred at room temperature for 30 minutes. To the reaction solution was added 8 ml (84 mmol) of tert-butanol, the mixture was heated under stirring at 100° C. for 2.5 hours and then the reaction solution was concentrated. The resulting residue was dissolved in ethyl acetate, washed with 0.1N hydrochloric acid, water and brine successively, dried over magnesium sulfate and concentrated to dryness. To the resulting residue was added a mixed solution of diethyl ether and hexane, and the resulting crystals were collected by filtration to give 7.87 g of the title compound.

$^1$H-NMR (DMSO-d$_6$) δ (ppm); 1.48(9H, s), 2.38(3H, s), 6.37–6.44(1H, m), 6.68(1H, d, J=8.4 Hz), 7.22–7.31(2H, m), 8.86(1H, brs), 10.73(1H, brs).

Production Example 10

7-(N-tert-Butoxycarbonyl)amino-3-formyl-4-methyl-1H-indole

To 400 ml (5.2 mol) of dimethylformamide was added 40 ml (429 mmol) of phosphorous oxychloride at 0° C. in a nitrogen atmosphere followed by stirring at the same temperature for 25 min. At 0° C., 74.0 g (300 mmol) of the compound of Production Example 9 was added thereto followed by stirring at room temperature for 1.5 hr. To the reaction mixture was added 250 ml of a 5N aqueous solution of sodium hydroxide under ice-cooling to adjust to pH8. Tetrahydrofuran, ethyl acetate and water were added thereto to separate the organic layer, followed by washing with water and brine successively. After drying over magnesium sulfate, the solvent was evaporated. To the resulting residue was added a mixed solution of diethyl ether and hexane, and the resulting crystals were collected by filtration to give 53.7 g of the title compound.

$^1$H-NMR (DMSO-d$_6$) δ (ppm); 1.50(9H, s), 2.71(3H, s), 6.90(1H, d, J=7.6 Hz), 7.32–7.41(1H, m), 8.21(1H, d, J=1.6 Hz), 8.99(1H, brs), 9.93(1H, s), 11.88(1H, brs).

Production Example 11

7-(N-tert-Butoxycarbonyl)amino-3-cyano-4-methyl-1H-indole

In 50 ml of dimethylformamide was dissolved 4.43 g (16.2 mmol) of the compound of Production Example 10 followed by adding 1.35 g (19.4 mmol) of hydroxylamine hydrochloride and 1.6 ml (19.8 mmol) of pyridine thereto. After heating under stirring at 60° C. for 45 min, 1,1'-carboyldiimidazole (80.8mmol) was added to the reaction solution under ice-cooling. After heating under stirring at 60° C. for further 30 min, 4.5 ml (32.3 mmol) of triethyl amine was added to the reaction solution followed by heating under stirring at the same temperature for further 30 min. Water was added to the reaction mixture under ice-cooling followed by extracting with ethyl acetate. The organic layer was washed with water and brine successively, dried over magnesium sulfate and then concentrated to give 4.27 g of the title compound.

$^1$H-NMR (DMSO-d$_6$) δ (ppm); 1.49 (9H, s), 2.60(3H, s), 6.89(1H, d, J=8.0 Hz), 7.34–7.42(1H, m), 8.20(1H, d, J=2.8 Hz), 9.04(1H, brs), 11.80(1H, brs).

Production Example 12

7-Amino-3-cyan)-4-methyl-1H-indole

Into a mixed solution of 100 ml of tetrahydrofuran and 100 ml of methanol were suspended 12.6 g (62.6 mmol) of the compound of Production Example 6, and hydrogenation was carried out at 3 atmospheric pressure and at ambient temperature in the presence of 430 mg (1.87 mmol) of platinum oxide. The filtrate was filtered off followed by concentrating to dryness, a mixed solution of tert-butyl methyl ether and hexane was added to the residue and the crystals were collected by filtration to give 10.7 g of the title compound. Into 400 ml of dichloromethane was dissolved 50.5 g (186 mmol) of the compound of Production Example 11 and 210 ml (2.76 mmol) of trifluoroacetic acid was added thereto at 0° C. in a nitrogen atmosphere followed by stirring at room temperature for 40 minutes. To the reaction solution was added a 5N aqueous solution of sodium hydroxide at −20° C. to adjust to pH 7. The solvent was removed and the residue was extracted with ethyl acetate. The organic layer was washed with water and brine successively, dried over magnesium sulfate and concentrated to dryness. A mixed solution of diethyl ether and hexane was added to the resulting residue and the crystals were collected by filtration to give 24.5 g of the title compound.

$^1$H-NMR (DMSO-d$_6$) δ (ppm); 2.47(3H, s), 5.07(2H, s), 6.34(1H, d, J=7.6 Hz), 6.64(1H, d, J=7.6 Hz), 8.10(1H, s), 11.70(1H, brs).

Production Example 13

3-(Cyanobenzenesulfonyl Chloride

To a mixed solution of 200 ml of water and 250 ml of concentrated hydrochloric acid was added 25.0 g (212 mmol) of 3-cyanoaniline followed by stirring. An aqueous solution (80 ml) of 15.5 g (223 mmol) of sodium nitrite was added dropwise thereinto at −10° C. The reaction solution was added to acetic acid saturated with sulfur dioxide (prepared by saturating sulfur dioxide in 250 ml of acetic acid followed by adding 2.1 g of cuprous chloride) under ice-cooling and stirring. After 1 hour, the reaction solution was poured onto 500 ml of ice water and extracted with diethyl ether. The extract was washed with a saturated aqueous solution of sodium bicarbonate, water and brine successively, and dried over magnesium sulfate. The solvent was evaporated, a mixed solution of diethyl ether and hexane was added to the residue and the crystals were collected by filtration to give 16.0 g of the title compound.

$^1$H-NMR (DMSO-d$_6$) δ (ppm); 7.55(1H, t, J=8.0 Hz), 7.78(1H, dd, J=8.0, 1.2 Hz), 7.86–7.92(2H,m).

Production Example 14

4-Sulfamoylbenzenesulfonyl Chloride

To a mixed solution of 80 ml water and 50 ml of concentrated hydrochloric acid was added 25.0 g (145 mmol) of 4-aminobenzenesulfonamide followed by stirring. An aqueous solution (20 ml) of 10.5 g (152 mmol) of sodium nitrite was added dropwise thereinto at −13° C. to −10° C. during 15 min. After 10 min, the reaction solution was added to a mixed solution saturated with sulfur dioxide (prepared by saturating sulfur dioxide in a mixed solution of 150 ml of acetic acid and 12.5 ml of concentrated hydrochloric acid followed by adding 3.7 g of cuprous chloride) at −30° C. under stirring. After 1 hr, 500 ml of ice water was added to the reaction solution, and the resulting precipitates were collected by filtration. The precipitates were dissolved in a mixed solution of 450 ml of toluene and 150 ml of ethyl acetate. After the resulting insoluble matters were filtered off, the filtrate was extracted with ethyl acetate. The organic layer was washed with a saturated sodium bicarbonate solution and brine successively, and dried over magnesium sulfate. The solvent was evaporated, 100 ml of toluene was added to the resulting residue and the crystals were collected by filtration to give 20.9 g of the title compound.

$^1$H-NMR (DMSO-$d_6$) δ (ppm); 7.65–7.69(2H,m), 7.71–7.78(4H,m).

Production Example 15

5-Bromo-3-chloro-7-nitro-1H-indole

To a solution of 12.00 g (49.8 mmol) of 5-bromo-7-nitro-1H-indole in 140 ml of tetrahydrofuran were added 1.4 ml of dimethylformamide and 6.98 g (52.3 mmol) of N-chlorosuccinimide followed by stirring at room temperature overnight. A 10% aqueous solution of sodium thiosulfate was added thereto followed by extracting with ethyl acetate. The organic layer was washed with water and brine successively, dried over magnesium sulfate and concentrated to dryness to give 14.84 g of the title compound.

$^1$H-NMR (DMSO-$d_6$) δ (ppm); 7.79(1H, s), 8.15(1H, s), 8.23(1H, s), 12.32(1H, brs).

Production Example 16

7-Amino-5-bromo-3-chloro-1H-indole Hydrochloride

To a solution (250 ml) of 14.84 g (53.9 mmol) of the compound of Production Example 15 in methanol were added 70 ml of concentrated hydrochloric acid and 31.97 g (269 mmol) of tin dust, followed by stirring at room temperature for 80 minutes. After a 5N aqueous solution of sodium hydroxide was added thereto under ice-cooling to adjust to pH 10, the resulting precipitates were filtered off and the filtrate was extracted with ethyl acetate. The organic layer was washed with a saturated sodium bicarbonate solution and brine successively, dried over magnesium sulfate and concentrated. Then, the resulting residue was purified by silica gel column chromatography to give 14.35 g of 7-amino-5-bromo-3-chloro-1H-indole. It was dissolved in ethyl acetate and a mixed solution (17 ml) of 4N hydrogen chloride and ethyl acetate was added thereto. The resulting precipitates were collected by filtration and washed with hexane to give 13.23 g of the title compound.

$^1$H-NMR (DMSO-$d_6$) δ (ppm); 5.11(3H, brs), 6.64(1H, s), 6.93(1H, s), 7.50(1H, d, J=2.0 Hz), 11.38(1H, brs).

Production Example 17

Ethyl pyruvate 2-(4-methyl-2-nitrophenyl) hydrazone

Into 110 ml of water was suspended 30.00 g (0.197 mol) of 4-methyl-2-nitroaniline followed by adding 66 ml of concentrated hydrochloric acid thereto. An aqueous solution (35 ml) of 16.33 g (0.237 mol) of sodium nitrite was added dropwise thereinto at 10° C. or below, followed by stirring for 40 minutes under ice-cooling to prepare a diazonium salt solution. In a mixed solution of 150 ml of ethanol and 300 ml of water was dissolved 28.43 g (0.197 mol) of ethyl 2-methylacetoacetate, followed by adding 120 ml of an aqueous solution of 53.36 g (0.808 mol) of potassium hydroxide thereto under ice-cooling. Then, the previously-prepared diazonium salt solution was added dropwise thereinto at the same temperature and stirred under ice-cooling for 20 minutes. After concentrated hydrochloric acid was added thereto to adjust to pH 1, the resulting precipitates were collected by filtration, washed with water and vacuum dried on phosphorus pentaoxide to give 46.42 g of the title compound.

$^1$H-NMR (DMSO-$d_6$) δ (ppm); 1.40(3H, t, J=7.2 Hz), 2.23(3H, s), 2.36(3H, s), 4.35(2H, q, J=7.2 Hz), 7.44(1H, dd, J=8.8, 1.6 Hz), 7.93(1H, d, J=8.8 Hz), 8.00(1H, s), 10.87 (1H, brs).

Production Example 18

Ethyl 5-methyl-7-nitro-1H-indole-2-carboxylate

To a solution (320 ml) of 15.92 g (60.0 mmol) of the compound of Production Example 17 in xylene was added polyphosphoric acid followed by heating under stirring overnight. Water and ethyl acetate were added thereto, the resulting insoluble matters were filtered off and the organic layer was separated. The organic layer was washed with water and brine successively, dried over magnesium sulfate and concentrated. Then, the resulting residue was purified by silica gel column chromatography to give 7.32 g of the title compound.

$^1$H-NMR (DMSO-$d_6$) δ (ppm); 1.34(3H, t, J=7.0 Hz), 2.47(3H, s), 4.36 (2H, q, J=7.0 Hz), 7.35 (1H, s), 7.99 (1H, s), 8.11 (1H, s), 11.25 (1H, brs).

Production Example 19

5-Methyl-7-nitro-1H-indole

To a solution (80 ml) of 7.86 g (31.7 mmol) of the compound of Production Example 18 in tetrahydrofuran was added 150 ml of a 1N aqueous solution of sodium hydroxide under ice-cooling followed by stirring at room temperature for 3.5 hr. Under ice-cooling, 2N hydrochloric acid was added thereto to adjust to pH1 followed by extracting with ethyl acetate. The organic layer was washed with water and brine successively, dried over magnesium sulfate and then concentrated to dryness to give 7.13 g of 5-methyl-7-nitro-1H-indole-2-carboxylic acid. The resulting compound was dissolved in 160 ml of 1,3-dimethyl-2-imidazolidinone followed by adding 716 mg (3.24 mmol) of basic copper carbonate and stirring at 185° C. for 2 hr. The reaction solution was poured into water, the resulting insoluble matters were filtered off, and the resulting filtrate was extracted with ethyl acetate. The organic layer was washed with water and brine successively, dried over magnesium sulfate and concentrated. Then, the resulting residue was purified by silica gel column chromatography to give 4.50 g of the title compound.

$^1$H-NMR (DMSO-$d_6$) δ (ppm); 2.46(3H, s), 6.62(1H, d, J=2.8 Hz), 7.47(1H, d, J=2.8 Hz), 7.87(1H, s), 7.92(1H, s), 11.77(1H, brs).

Production Example 20

3-Bromo-5-methyl-7-nitron-1H-indole

To a solution (70 ml) of 4.50 g (25.5 mmol) of the compound of Production Example 19 in tetrahydrofuran were added 0.7 ml of dimethylformamide and 4.78 g (26.9 mmol) of N-bromosuccinimide, followed by stirring at room temperature for 70 min. A 10% aqueous solution of sodium thiosulfate was added thereto followed by extracting with ethyl acetate. The organic was washed with water and brine successively, dried over magnesium sulfate and then concentrated to dryness to give 6.53 g of the title compound.

$^1$H-NMR (DMSO-d$_6$) δ (ppm); 2.50(3H, s), 7.67(1H, s), 7.73(1H, s), 8.02(1H, s), 12.10(1H, brs).

Production Example 21

7-Amino-3-bromo-5-methyl-1H-indole

Into a mixed solution of 150 ml of methanol and 75 ml of water was suspended 6.76 g (26.5 mmol) of the compound of Production Example 20, and then 11.34 g (212 mmol) of ammonium chloride and 5.92 g (106mmol) of iron powder were added thereto. After stirring at 80° C. for 1 hour, the resulting insoluble matters were filtered off. A saturated sodium bicarbonate solution was added to the filtrate to adjust to pH 8 followed by extracting with ethyl acetate.

The organic layer was washed with a saturated sodium bicarbonate solution, water and brine successively, dried over magnesium sulfate and concentrated. Then, the resulting residue was purified by silica gel column chromatography to give 3.30 g of the title compound.

$^1$H-NMR (DMSO-d$_6$), δ (ppm); 2.24(3H, s), 5.08(2H, brs), 6.20(1H, s), 6.41(1H, s), 7.35(1H, s), 10.86(1H, brs).

Production Example 22

6-Amino-3-pyridinesulfonyl Chloride

To 123.8 g (1.06 mol) of chlorosulfonic acid was added 10.00 g (0.106 mol) of 2-aminopyridine by portions under ice-cooling. Thionyl chloride (50.56 g, 0.425 mol) was added thereto, followed by heating under reflux for 2.5 hours and further stirring at 150° C. for 7 hours. The reaction solution was poured onto ice water, neutralized by adding sodium bicarbonate thereto and extracted with ethyl acetate. The organic layer was washed with a saturated sodium bicarbonate solution, water and brine successively, dried over magnesium sulfate and then concentrated to dryness. The resulting residue was suspended in ethyl ether and the insoluble matters were filtered off. The filtrate was concentrated to dryness and the resulting residue was recrystallized from ethyl ether-hexane to give 6.58 g of the title compound.

Production Example 23

4,7-Dibromo-1H-indole

From 62.0 g (0.224 mol) of 2,5-dibromonitrobenzene was obtained 27.2 g of the title compound by the same manner as in Production Example 1 of JP-A 7-165708.

$^1$H-NMR (DMSO-d$_6$) δ (ppm); 6.52(1H, d, J=3.2 Hz), 7.18 (1H,d,J=8.0 Hz), 7.26 (1H, d,J=8.0 Hz), 7.53 (1H, d, J=3.2 Hz), 11.75(1H, brs).

Production Example 24

7-Amino-4-bromo-1H-indole Hydrochloride

Into a solution (300 ml) of 27.2 g (98.9 mmol) of the compound of Production Example 23 in tetrahydrofuran was added dropwise 186 ml (116.3 mmol) of a 1.6M solution of n-butyl lithium in hexane in a nitrogen atmosphere at −78° C. followed by stirring for 1 hour under ice-cooling. After cooling again to −78° C., 28 ml (0.13 mmol) of diphenylphosphoryl azide was added dropwise thereinto and the mixture was stirred at −78° C. for 1 hour and then at −40° C. for 1 hour. After adding 150 g of a 3.4M solution of sodium bis(2-methoxyethoxy)aluminum hydride in toluene thereto at −40° C., it was stirred at room temperature for 1 hour. Water (120 ml) was added thereto, the resulting insoluble matters were collected by filtration and the filtrate was extracted with ethyl ether. The organic layer was washed with a saturated sodium bicarbonate solution and brine successively, and dried over magnesium sulfate. After it was concentrated, the resulting residue was dissolved in ethyl ether, 50 ml of a mixed solution of 4N hydrochloric acid and ethyl acetate was added thereto, and the resulting precipitates were collected by filtration to give 14.5 g of the title compound.

$^1$H-NMR (DMSO-d$_6$) δ (ppm); 6.41–6.43(1H, m), 6.80 (1H,d,J=8.0 Hz), 7.16(1H,d,J=8.0 Hz), 7.54(1H, t, J=2.8 Hz), 11.57(1H, brs).

Production Example 25

7-Bromo-4-chloro-1H-indole

The title compound was obtained by the same manner as in Production Example 23.

$^1$H-NMR (DMSO-d$_6$) δ (ppm); 6.60–6.61(1H, m), 7.04 (1H, d, J=8.1 Hz), 7.32(1H,d,J=8.1 Hz), 7.53(1H, t,J=2.7 Hz), 11.74(1H, brs).

Production Example 26

7-Amino-4-chloro-1H-indole Hydrochloride

The title compound was obtained by the same manner as in Production Example 24.

$^1$H-NMR (DMSO-d$_6$) δ (ppm); 6.54–6.55(1H, m), 7.05 (1H, d, J=8.1 Hz), 7.11(1H, d, J=8.1 Hz), 7.60(1H, t, J=2.7 Hz), 11.82(1H, brs).

Production Example 27

9-Bromo-2-thiophenecarhoxy Aldehyde

To a solution (80 ml) of 10.0 g (41.3 mmol) of 5-dibromothiophene in tetrahydrofuran was added dropwise 27.0 ml (43.4 mmol) of a 1.6M solution of n-butyllithium in hexane in a nitrogen atmosphere at −78° C., followed by stirring at the same temperature for 10 min. Then, 3.5 ml (45.5 mmol) of dimethylformamide was added thereto at the same temperature, followed by stirring for 20 min. Water was added thereto, followed by extracting with ethyl acetate. The organic layer was washed with a 0.1N aqueous solution of hydrochloric acid, water and brine successively, and dried over magnesium sulfate. It was concentrated to dryness to give 6.4 g of the title compound.

$^1$H-NMR (DMSO-d$_6$) δ (ppm); 7.49(1H, d, J=4.0 Hz), 7.87(1H, d, J=3.9 Hz), 9.81(1H, s).

Production Example 28

9-Bromo-2-thiophene Carbonitrile

To a solution of 8.2 g (43.1 mmol) of the compound of Production Example 27 in 40 ml of dimethylformamide were added 3.3 g (51.7 mmol) of hydroxylamine hydrochloride and 4.1 g (51.7 mmol) of pyridine followed by stirring at room temperature for 30 minutes. Then, 34.9 g (215.5 mmol) of 1,1'-carbonyldiimidazole were added thereto under ice-cooling followed by stirring at room temperature for 1 hour. Ice water was added to the reaction solution followed by extracting with ethyl acetate. The organic layer was washed with a 0.1N aqueous solution of hydrochloric acid, water and brine successively, and dried over magnesium sulfate. After it was concentrated, the resulting residue was purified by a silica gel column chromatography to give 6.7 g of the title compound.

$^1$H-NMR (DMSO-$d_6$) δ (ppm); 7.45(1H, d, J=4.0 Hz), 7.84(1H, d, J=4.0 Hz).

Production Example 29

5-Benzylthio-2-thiophene Carbonitrile

Into 10 ml of dimethyl sulfoxide was suspended 585 mg (13.4 mmol; 55% oily) of sodium hydride, and then 1.4 g (11.2 mmol) of benzylmercaptan was added thereto under ice-cooling, followed by stirring for 10 minutes. Then 2.1 g (11.2 mmol) of the compound of Production Example 14 were added thereto followed by stirring at room temperature for 1 hour. Water was added to the reaction solution followed by extracting with ethyl acetate. The organic layer was washed with water and brine successively and dried over magnesium sulfate. After it was concentrated, the resulting residue was purified by silica gel column chromatography to give 1.51 g of the title compound.

$^1$H-NMR (DMSO-$d_6$) δ (ppm); 4.26(2H, s), 7.18(1H, d, J=4.0 Hz), 7.27–7.30(5H,m), 7.83(1H,d,J=4.0 Hz).

Production Example 30

4-Bromo-1H-indole Carboxylic Acid

From 51 g of the compound of Production Example 23 was obtained 34 g of the title compound by the same manner as in Production Example 8.

$^1$H-NMR (CDCl$_3$) δ (ppm); 6.51–6.52(1H, m), 7.35(1H, d, J=8.0 Hz), 7.48(1H, t, J=2.8 Hz), 7.66(1H, d, J=8 Hz), 11.4(1H, brs), 13.2 (1H, brs).

Production Example 31

7-(N-tert -Butoxycarbonyl)amino-4-bromo-1H-indole

From 34 g of the compound of Production Example 30 was obtained 32 g of the title compound by the same manner as in Production Example 9.

$^1$H-NMR (CDCl$_3$) δ (ppm); 1.51(9H, s), 6.38–6.39(1H, m), 7.13(1H, d, J=8.0 Hz), 7.44–7.46(2H, m), 9.11(1H, brs), 11.2(1H, brs).

Production Example 32

7-tert-Butoxycarbonyl)amine-4-bromo-3-1H-indole

The title compound was obtained by treating with N-chlorosuccinimide in a solution of the compound of Production Example 31 in tetrahydrofuran/dimethylformamide.

$^1$H-NMR (CDCl$_3$) δ (ppm); 1.50(9H, s), 7.19(1H,d,J=8.4 Hz), 7.45(1H,d,J=8.4 Hz), 7.62(1H,d,J=2.8 Hz), 9.08(1H, brs), 11.41(1H, brs).

Production Example 33

7-Amino-4-bromo-3-chloro-1H-indole Hydrochloride

The compound (10.87 g, 31.5 mmol) of Production Example 32 was dissolved in 120 ml of methanol, and 20 ml of concentrated hydrochloric acid was added thereto followed by stirring at 60° C. for 40 minutes. After completion of the reaction, the solvent was removed and the resulting residue was subjected to an azeotropic distillation for three times with ethanol. The resulting residue was washed with ether to give 8.5 g of the title compound.

$^1$H-NMR (CDCl$_3$) δ (ppm); 6.67 (1H,d,J=8.0 Hz), 7.13 (1H, d, J=8.0 Hz), 7.65(1H,d,J=2.8 Hz), 11.74(1H, brs).

Production Example 34

2-Amino-5-pyrimidine Sulfonyl Chloride

In ice-water, 21 ml (0.316 mol) of chlorosulfonic acid was cooled and 3 g (0.032 mol) was added thereto by portions under stirring. Further, 9.2 ml (0.126 mol) of thionyl chloride was added thereto followed by stirring at 150° C. for 70 hours. The reaction solution was returned to room temperature and poured on water and the mixture was extracted with ethyl acetate. The extract was dried over sodium sulfate and concentrated to dryness to give 1.7 g of the title compound.

$^1$H-NMR (CDCl$_3$) δ (ppm); 5.97(2H, broad), 8.83(2H, s).

EXAMPLE 1

3-Cyano-N-(3-cyano-4-methyl-1H-indol-7-yl)benzenesulfonamide

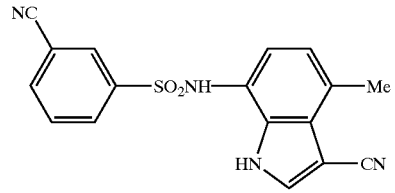

The compound (2.00 g, 11.7 mmol) of Production Example 12 was dissolved in 60 ml of tetrahydrofuran, and then 4.0 ml (49.5 mmol) of pyridine and 2.60 g (12.9 mmol) of the compound of Production Example 13 were added thereto. After stirring at room temperature for 16 hr, a 2N hydrochloric acid was added thereto to adjust to pH 1–2, and the mixture was extracted with ethyl acetate. The organic layer was washed with water and brine successively, dried over magnesium sulfate and concentrated. Then, the resulting residue was purified by silica gel column chromatography to give 3.90 g of the title compound.

m.p.: 220–221° C. (recrystallized from ethanol/n-hexane)

$^1$H-NMR (DMSO-$d_6$) δ (ppm); 2.55(3H,s), 6.50(1H,d,J= 8.0 Hz), 6.77(1H,d,J=8.0 Hz), 7.71(1H, t, J=8.0 Hz), 7.90 (1H, d, J=8.0 Hz), 8.05–8.13(2H, m), 8.16(1H, s), 10.11(1H, brs), 12.01(1H, brs).

EXAMPLE 2

6-Chloro-N-(3-cyano-4-methyl-1H-indole-7-yl)-3-pyridinesulfonamide

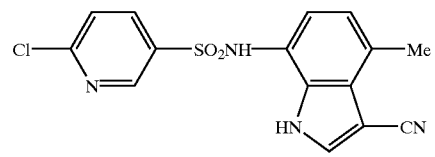

The compound (700 mg, 4.09 mmol) of Production Example 12 was dissolved in 20 ml of tetrahydrofuran, and then 1.3 ml (16.1 mmol) of pyridine and 950 mg (4.48 mmol) of 6-chloro-3-pyridinesulfonylchloride were added thereto. After stirring at room temperature for 2 hours, a 1N hydrochloric acid was added thereto to adjust to pH 1–2 and the mixture was extracted with ethyl acetate. The organic layer was washed with water and brine successively, dried over magnesium sulfate and concentrated. Then, the resulting residue was purified by silica gel column chromatography to give 1.16 g of the title compound.

m.p.: 262–2630° C. (recrystallized from ethanol/hexane)

$^1$H-NMR (DMSO-$d_6$) δ (ppm); 2.57(3H, s), 6.55(1H,d, J=7.6 Hz), 6.82(1H,d,J=7.6 Hz), 7.69(1H,d,J=8.4 Hz), 8.01 (1H, dd, J=8.4,2.4 Hz), 8.17(1H, d, J=2.8 Hz), 8.60(1H, d, J=2.4 Hz), 10.21(1H, brs), 12.03(1H, brs).

EXAMPLE 3

N-(3-Bromo-5-methyl-1H-indole-7-yl)-4-sulfamoylbenzenesulfonamide

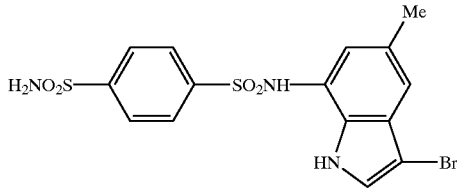

The compound (200 mg, 0.89 mmol) of Production Example 22 was dissolved in 6 ml of tetrahydrofuran, and then 0.3 ml (3.71 mmol) of pyridine and 300 mg (1.17 mmol) of the compound of Production Example 14 were added thereto. After stirring at room temperature for 48 hr, a 1N hydrochloric acid was added thereto to adjust pH to 1–2 and the mixture was extracted with ethyl acetate. The organic layer was washed with water and brine successively, dried over magnesium sulfate and concentrated. Then, a mixed solution of diethyl ether and hexane was added to the resulting residue and crystals were collected by filtration to give 387 mg of the title compound.

m.p.: 196–197° C. (recrystallized from ethanol/n-hexane)

$^1$H-NMR (DMSO-$d_6$) δ (ppm); 2.24(3H,s), 6.60(1H,s), 6.98(1H, s), 7.44(1H,s), 7.55(2H, brs), 7.85–7.95(4H,m), 10.13(1H, brs), 11.01(1H, brs).

EXAMPLE 4

6-Amino-N-(5-bromo-3-chloro-1H-indole-7-yl)-3-pyridinesulfonamide

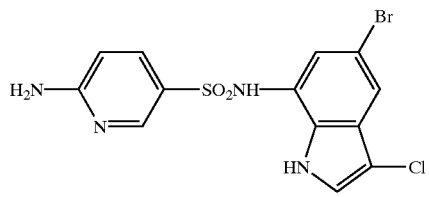

The compound (1.00 g, 3.55 mmol) of Production Example 16 was suspended in 25 ml of tetrahydrofuran, and then 0.86 ml (10.6 mmol) of pyridine and 718 mg (3.73 mmol) of the compound of Production Example 8 were added thereto under ice-cooling. After stirring at room temperature for 3 hours, water was added thereto and the mixture was extracted with ethyl acetate. The organic layer was washed with water and brine successively, dried over magnesium sulfate and concentrated. Then, the resulting residue was purified by silica gel column chromatography to give 1.27 g of the title compound.

m.p.: It began to color at near 237° C. and decomposed at 240–242° C. (recrystallized from ethanol-water)

$^1$H-NMR (DMSO-$d_6$) δ (ppm); 6.37(1H, d, J=8.8 Hz), 6.94(2H, brs), 6.97(1H, s), 7.36(1H, s), 7.54–7.57(2H,m), 8.16(1H,d,J=2.8 Hz), 9.94(1H, brs), 11.17(1H, brs).

Hydrochloride: $^1$H-NMR (DMSO-$d_6$) δ (ppm); 6.59(1H, d, J=9.2 Hz), 7.00(1H, s), 7.40(1H, s), 7.56(1H, d, J=2.4 Hz), 7.70(1H, dd, J=9.2, 2.0 Hz), 8.20(1H, d, J=2.0 Hz), 10.20 (1H, brs), 11.37(1H, brs).

EXAMPLE 5

N-(3-Bromo-5-methyl-1H-indole-7-yl)-3-cyanobenzenesulfonamide

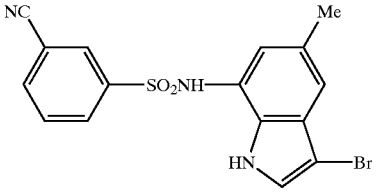

To a solution (6 ml) of 260 mg (1.16 mmol) of the compound of Production Example 21 in tetrahydrofuran were added 0.19 ml (2.35 mmol) of pyridine and 280 mg (1.39 mmol) of 3-cyanobenzenesulfonyl chloride under ice-cooling, and the mixture was stirred at room temperature overnight. A 0.2N hydrochloric acid was added thereto, and the mixture was extracted with ethyl acetate. The organic layer was washed with water and brine successively, dried over magnesium sulfate and concentrated. Then, the resulting residue was purified by silica gel column chromatography to give 360 mg of the title compound.

m.p.: It began to decompose at near 148° C. and decomposed rapidly at 163–164° C. (recrystallized from ethanol-n-hexane)

$^1$H-NMR (DMSO-$d_6$) δ (ppm); 2.25(3H, s), 6.54(1H, s), 7.01(1H, s), 7.42(1H, d, J=2.8 Hz), 7.71(1H, t, J=7.6 Hz), 7.93(1H, d, J=7.6 Hz), 8.07–8.11(2H,m), 10.09(1H, brs), 11.04(1H, brs).

EXAMPLE 6

N-(4-Bromo-1H-indole-7-yl)-4-cyanobenzenesulfonamide

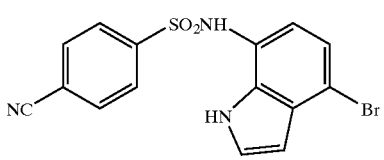

The title compound (686 mg) was obtained by treating 700 mg (2.8 mmol) of the compound of Production Example 24 and 685 mg (3.4 mmol) of 4-cyanobenzenesulfonylchloride in the same manner as in Example 1.

m.p.: 214–216° C.

¹H-NMR (DMSO-d₆) δ (ppm); 6.35(1H, d, J=2.6 Hz), 6.53(1H,d,J=8.0 Hz), 7.04(1H,d,J=8.0 Hz), 7.41(1H,t,J=2.8 Hz), 7.85(2H,d,J=8.0 Hz), 8.00 (2H,d,J=8.0 Hz), 10.24(1H, brs), 11.19(1H, brs).

EXAMPLE 7

6Amino-N-(4-chloro-1H-indole-7-yl)-3pyridinesulfonamide

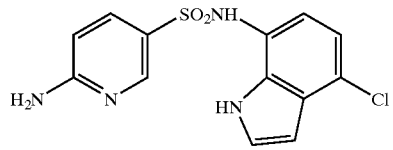

The title compound (961 mg) was obtained by treating 1330 mg (6.4 mmol) of the compound of Production Example 22 and 1000 mg (4.9 mmol) of the compound of Production Example 12 in the same manner as in Example 1.

m.p.: 204–206° C.

¹H-NMR (DMSO-d₆) δ (ppm); 6.38(1H,d,J=9.0 Hz), 6.43 (1H,t,J=2.2 Hz), 6.77(1H,d,J=7.7 Hz), 6.86(2H, brs), 7.42 (1H,t,J=2.6 Hz), 7.56(1H,dd,J=2.6, 9.0 Hz), 8.14(1H,d,J=2.6 Hz), 9.70(1H, brs), 11.07(1H, brs).

EXAMPLE 8

6-Amino-N-(3-bromo-4-chloro-1H-indole-7-yl)-3-pyridinesulfonamide and Hydrochloride Thereof

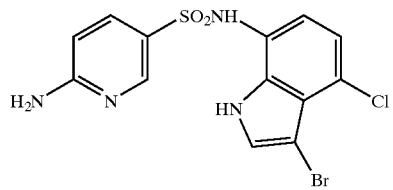

To a solution (10 ml) of 650 mg (2.0 mmol) of the compound of Example 7 in tetrahydrofuran were added 1 ml of dimethylformamide and 359 mg (2.0 mmol) of N-bromosuccinimide followed by stirring at room temperature overnight. A 0.2N aqueous solution of hydrochloric acid was added thereto followed by extracting with ethyl acetate. The organic layer was washed with an aqueous solution of sodium thiosulfate, water and brine successively, dried over magnesium sulfate and concentrated. Then, the resulting residue was purified by silica gel column chromatograhy to give 662 mg of the title compound.

¹H-NMR (DMSO-d₆) δ (ppm); 6.38(1H,d,J=8.8 Hz), 6.76 (1H,d,J=8.4 Hz), 6.88(2H, brs), 6.97(1H,d,=8.4 Hz), 7.52–7.56(2H,m) 8.12(1H,d,J=2.4 Hz), 9.68(1H, brs), 11.44 (1H, brs).

In 3 ml of acetone was dissolved 660 mg of the resulting title compound, 0.62 ml of a 4N hydrochloric acid in ethyl acetate was added thereto and the resulting precipitates were collected by filtration to give 590 mg of a hydrochloride of the title compound.

m.p.: It gradually began to decompose at near 267° C.

¹H-NMR (DMSO-d₆) δ (ppm); 6.65(1H,d,J=9.2 Hz), 6.78 (1H,d,J=8.1 Hz), 6.98(1H,d,J=8.2 Hz), 7.57(1H,d,J=2.6 Hz), 7.73(1H,dd,J=2.0, 9.0 Hz), 8.15(1H,d,J=2.4 Hz), 10.00(1H, brs), 11.67(1H, brs).

EXAMPLE 9

N-(3-Bromo-5-methyl-1H-indole-7-yl)-5-cyano-2-thiophenesulfonamide

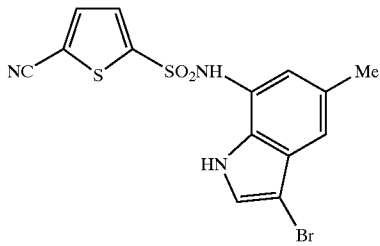

Into a solution of 1.3 g (5.6 mmol) of the compound of Production Example 29 in 15 ml of concentrated hydrochloric acid (15 ml) was introduced chlorine gas under ice-cooling. After stirring for 30 minutes, the reaction solution was added to ice-water followed by extracting with ethyl acetate. The organic layer was washed with water and brine successively, dried over magnesium sulfate and concentrated. The resulting residue was added to a solution of 1.2 g (5.35 mmol) of the compound of Production Example 22 in 6 ml of pyridine followed by stirring at room temperature overnight. Water was added thereto followed by extracting with ethyl acetate. The organic layer was washed with a 1N aqueous solution of hydrochloric acid, water and brine successively, dried over magnesium sulfate and concentrated. Then, the residue was purified by silica gel column chromatography to give 1227 mg of the title compound.

m.p.: 166–169° C. (decomposition)

¹H-NMR (DMSO-d₆) δ (ppm); 2.30(3H,s), 6.65(1H, s), 7.07(1H,s), 7.44(1H,s), 7.54(1H,d,J=4.0 Hz), 7.94(1H,d,J= 4.0 Hz), 10.47(1H, brs), 11.04(1H, brs).

EXAMPLE 10

2-Amino-N-(4-bromo-3-chloro-1H-indole-7-yl)-5-pyrimidinesulfonamide

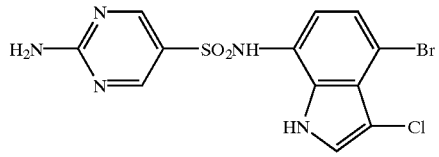

To a 5 ml solution of 712 mg (2.52 mmol) of the compound of Production Example 33 in pyridine was added 513 mg (2.65 mmol) of the compound of Production Example 34, and the mixture was stirred for 15 hours. Water was added to the reaction solution, and then it was extracated with a mixed solution of ethyl acetate and tetrahydrofuran (10:1). The organic layer was dried over magnesium sulfate, and then concentrated and purified by silica gel column chromatography to give 950 mg of the title compound.

m.p.: 285–289° C.

¹H-NMR (DMSO-d₆) δ (ppm); 6.75(1H,d,J=8.0 Hz), 7.19 (1H,d,J=8.0 Hz), 7.59(1H, d, J=3.0 Hz), 7.65(2H,s), 8.37 (2H,s), 9.82(1H,s), 11.43(1H,s).

What is claimed:

1. An indole compound represented by the following formula (I), its pharmacologically acceptable salt thereof or hydrates thereof:

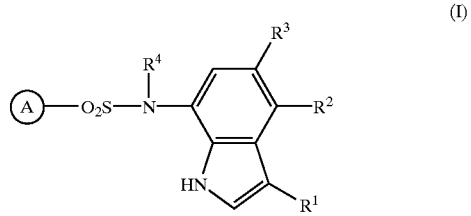

wherein
- $R^1$ represents hydrogen atom, a halogen atom or cyano group;
- $R^2$ and $R^3$ are the same as or different from each other and each represents a hydrogen atom, a $C_1$–$C_4$ lower alkyl group or a halogen atom;
- $R^4$ represents a hydrogen atom or a $C_1$–$C_4$ lower alkyl group;
- the ring A represents a cyanophenyl group, an aminosulfonylphenyl group, or a cyanothiophenyl group; and
wherein (i) all of $R^1$, $R^2$ and $R^3$ are not hydrogen atoms, (ii) both $R^2$ and $R^3$ are not hydrogen atoms, (iii) the ring A is not aminosulfonylphenyl group when both $R^1$ and $R^2$ are halogen atoms, and (iv) when the ring A is a cyanophenyl group and $R^1$ is a cyano group or a halogen group, at least one of $R^2$ and $R^3$ is not a hydrogen atom.

2. The indole compound as claimed in claim 1, its pharmacologically acceptable salt or hydrates thereof, wherein two of $R^1$, $R^2$ and $R^3$ are not hydrogen atoms.

3. The indole compound as claimed in claim 1 or 2, its pharmacologically acceptable salt or hydrates thereof, wherein the ring A is cyanophenyl group or aminosulfonylphenyl group.

4. The indole compound as claimed in claim 1 or 2, its pharmacologically acceptable salt or hydrates thereof, wherein the ring A is cyanothiophenyl group.

5. The indole compound as claimed in claim 1 or 2, its pharmacologically acceptable salt or hydrates thereof, wherein the ring A is cyanophenyl group.

6. The indole compound as claimed in claim 1, its pharmacologically acceptable salt thereof or hydrates thereof, said indole compound is selected from the group consisting of:
1) 3-Cyano-N-(3-cyano-4-methyl-1H-indol-7-yl)benzenesulfonamide,
2) N-(3-bromo-5-methyl-1H-indole-7-yl)-4-sulfamoylbenzenesulfonamide,
3) N-(3-bromo-5-methyl-1H-indole-7-yl)-3-cyanobenzenesulfonamide,
4) N-(4-bromo-1H-indole-7-yl)-4-cyanobenzenesulfonamide, and
5) N-(3-bromo-5-methyl-1H-indole-7-yl)-5-cyano-2-thiophenesulfonamide.

7. The indole compound as claimed in claim 1, its pharmacologically acceptable salt thereof or hydrates thereof, said indole compound is selected from the group consisting of:
1) 3-Cyano-N-(3-cyano-4-methyl-1H-indol-7-yl)benzenesulfonamide,
2) N-(3-bromo-5-methyl-1H-indole-7-yl)-4-sulfamoylbenzenesulfonamide,
3) N-(3-bromo-5-methyl-1H-indole-7-yl)-3-cyanobenzenesulfonamide, and
4) N-(3-bromo-5-methyl-1H-indole-7-yl)-5-cyano-2-thiophenesulfonamide.

8. An antiangiogenic composition which comprises a pharmacologically effective dose of the indole compound as claimed in claim 1, its pharmacologically acceptable salt of or hydrates thereof.

9. An antitumor composition for pancreatic, colon, gastric, breast, prostate, lung, or ovarian cancer, said antitumor composition comprising a pharmacologically effective dose of the indole compound in claim 1, its pharmacologically acceptable salt thereof or hydrates thereof.

10. A therapeutic composition for pancreatic cancer which comprises the indole compound as claimed in claim 1, its pharmacologically acceptable salt thereof or hydrates thereof in an effective amount.

11. A therapeutic composition for cancer of the colon which comprises the indole compound as claimed in claim 1, its pharmacologically acceptable salt thereof or hydrates thereof in an effective amount.

12. A therapeutic composition for gastric cancer which comprises the indole compound as claimed in claim 1, its pharmacologically acceptable salt thereof or hydrates thereof in an effective amount.

13. A therapeutic composition for breast cancer which comprises the indole compound as claimed in claim 1, its pharmacologically acceptable salt thereof or hydrates thereof in an effective amount.

14. A therapeutic composition for prostatic cancer which comprises the indole compound as claimed in claim 1, its pharmacologically acceptable salt thereof or hydrates thereof in an effective amount.

15. A therapeutic composition for lung cancer which comprises the indole compound as claimed in claim 1, its pharmacologically acceptable salt thereof or hydrates thereof in an effective amount.

16. A therapeutic composition for ovarian cancer which comprises the indole compound as claimed in claim 1, its pharmacologically acceptable salt thereof or hydrates thereof in an effective amount.

17. A composition for suppressing metastasis of cancer which comprises the indole compound as claimed in claim 1, its pharmacologically acceptable salt thereof or hydrates thereof in an effective amount.

18. A therapeutic composition for diabetic retinopathy which comprises the indole compound as claimed in claim 1, its pharmacologically acceptable salt thereof or hydrates thereof in an effective amount.

19. A therapeutic composition for rheumatic arthritis which comprises the indole compound as claimed in claim 1, its pharmacologically acceptable salt thereof or hydrates thereof in an effective amount.

20. A therapeutic composition for hematoma which comprises the indole compound as claimed in claim 1, its pharmacologically acceptable salt thereof or hydrates thereof in an effective amount.

21. A method for treating a disease in a patient in need thereof against which an inhibitory effect of antiogenesis at the site of a tumor, hematoma, rheumatic arthritis or diabetic retinopathy is effective for the treatment thereof, by administering an effective amount of the indole compound as claimed in claim 1, its pharmacologically acceptable salt thereof or hydrates thereof to said patient.

22. The method as claimed in claim 21, wherein the tumor is pancreatic, colon, gastric, breast, prostate, lung, or ovarian.

* * * * *